(12) United States Patent
Bailey et al.

(10) Patent No.: US 9,410,976 B2
(45) Date of Patent: Aug. 9, 2016

(54) PROCESS ANALYTIC INSTRUMENT WITH ENCAPSULATED FLAME-QUENCHING CONNECTION

(71) Applicant: Rosemount Analytical Inc., Houston, TX (US)

(72) Inventors: Edward J. Bailey, Cypress, TX (US); Jason P. Pratt, Cypress, TX (US); Vicente Ramirez, Jr., Houston, TX (US)

(73) Assignee: ROSEMOUNT ANALYTICAL INC., Houston, TX (US)

( * ) Notice: Subject to any disclaimer, the term of this patent is extended or adjusted under 35 U.S.C. 154(b) by 571 days.

(21) Appl. No.: 13/826,678

(22) Filed: Mar. 14, 2013

(65) Prior Publication Data

US 2014/0102171 A1 Apr. 17, 2014

Related U.S. Application Data

(63) Continuation-in-part of application No. 13/653,572, filed on Oct. 17, 2012, now Pat. No. 9,291,635.

(51) Int. Cl.
| | |
|---|---|
| *G01N 35/10* | (2006.01) |
| *G01N 33/00* | (2006.01) |
| *G01N 30/16* | (2006.01) |
| G01N 35/00 | (2006.01) |
| G01N 30/88 | (2006.01) |
| G01N 1/00 | (2006.01) |

(52) U.S. Cl.
CPC ............ *G01N 35/1095* (2013.01); *G01N 30/16* (2013.01); *G01N 33/0009* (2013.01); *G01N 35/1074* (2013.01); *G01N 2001/002* (2013.01); *G01N 2030/8881* (2013.01); *G01N 2035/00237* (2013.01)

(58) Field of Classification Search
CPC ............... G01N 2001/002; G01N 2030/8881; G01N 35/1074; G01N 35/1095; G01N 2035/00237
See application file for complete search history.

(56) References Cited

U.S. PATENT DOCUMENTS

| | | |
|---|---|---|
| 4,088,436 A | 5/1978 | Alferes |
| 4,302,136 A | 11/1981 | Abe et al. |
| 5,287,746 A | 2/1994 | Broden |

(Continued)

FOREIGN PATENT DOCUMENTS

| | | |
|---|---|---|
| CN | 1077531 | 10/1993 |
| CN | 2366668 Y | 3/2000 |

OTHER PUBLICATIONS

First Office Action from Chinese Patent Application No. 201410072150.3 dated Apr. 20, 2015, 17 pages with English Translation.

(Continued)

*Primary Examiner* — Paul West
(74) *Attorney, Agent, or Firm* — Christopher R. Christenson; Kelly, Holt & Christenson, PLLC

(57) ABSTRACT

A process analytic instrument and tube carrier are provided. The process analytic instrument includes an analytic module having a plurality of inlets and configured to analyze a process gas. The tube carrier is coupled to the analytic module and has a shell defining an interior therein. A plurality of tubes terminates in the tube carrier. At least one of the tubes has an integral flame-quenching pathway and the interior of the shell proximate the integral flame-quenching pathway is filled with a solid.

18 Claims, 2 Drawing Sheets

(56) References Cited

U.S. PATENT DOCUMENTS

| | | | |
|---|---|---|---|
| 5,746,976 | A | 5/1998 | Yamada et al. |
| 6,029,499 | A | 2/2000 | Sittler et al. |
| 6,212,958 | B1 * | 4/2001 | Conley ............... G01F 1/28 73/861.71 |
| 7,014,222 | B1 | 3/2006 | Poppe |
| 7,150,194 | B2 | 12/2006 | Pepperling et al. |
| 7,681,456 | B2 | 3/2010 | Hausler |
| 2002/0069758 | A1 * | 6/2002 | Burban ............... B01D 53/268 96/8 |
| 2004/0170531 | A1 | 9/2004 | Mueller |
| 2005/0118068 | A1 | 6/2005 | Kahl |
| 2006/0042686 | A1 | 3/2006 | Gamache et al. |
| 2008/0072976 | A1 | 3/2008 | Bailey et al. |
| 2013/0098140 | A1 | 4/2013 | Bailey et al. |

OTHER PUBLICATIONS

Second Office Action from Chinese Patent Application No. 201280003692.4, issuing date: Jan. 15, 2015, 14 pages with English Translation.

International Search Report and Written Opinion from International application No. PCT/US2012/060517, date of filing: Oct. 17, 2012. 11 pages.

First Office Action from Chinese patent application No. 201280003692.4, issuing date: Apr. 23, 2014. 19 pages with English translation.

Third Office Action for Chinese Patent Application No. 201280003692.4, dated Jul. 14, 2015, 19 pages.

Second Office Action for Chinese Patent Application No. 201410072150.3, dated Nov. 23, 2015, 20 pages with English Translation.

* cited by examiner

PROCESS ANALYTIC INSTRUMENT WITH ENCAPSULATED FLAME-QUENCHING CONNECTION

CROSS-REFERENCE TO RELATED APPLICATION

The present application is a Continuation-In-Part Application based on and claiming the benefit of U.S. patent application Ser. No. 13/653,572, filed Oct. 17, 2012, the content of which is hereby incorporated by reference in its entirety.

BACKGROUND

Process analytic sensors and instruments are employed in a variety of industries to measure and control gasses and liquids within the process. Process analyzers include, without limitation, process gas chromatographs, process gas analyzers, process hydrocarbon analyzers, continuous emission monitoring systems (CEMS), and the like.

Process analytic instruments, such as gas chromatographs and complex gas and/or liquid analyzers or instruments often require one or more connections to various gases, fluids, air, or vent lines. In gas analysis equipment designed to operate in hazardous/explosive environments, it is often necessary to provide a means by which gas may enter the equipment for analysis without allowing for a flame to propagate through the gas flow path. This situation would be necessary when the analysis equipment is disposed within an explosion-proof enclosure "Exd." Flame arrestors, which would normally provide the required flame quenching functions are often costly and can add significant cost to the instrument.

SUMMARY

A process analytic instrument and tube carrier are provided. The process analytic instrument includes an analytic module having a plurality of inlets and configured to analyze a process gas. The tube carrier is coupled to the analytic module and has a shell defining an interior therein. A plurality of tubes terminates in the tube carrier. At least one of the tubes has an integral flame-quenching pathway and the interior of the shell proximate the integral flame-quenching pathway is filled with a solid.

DETAILED DESCRIPTION OF ILLUSTRATIVE EMBODIMENTS

Figure 1:
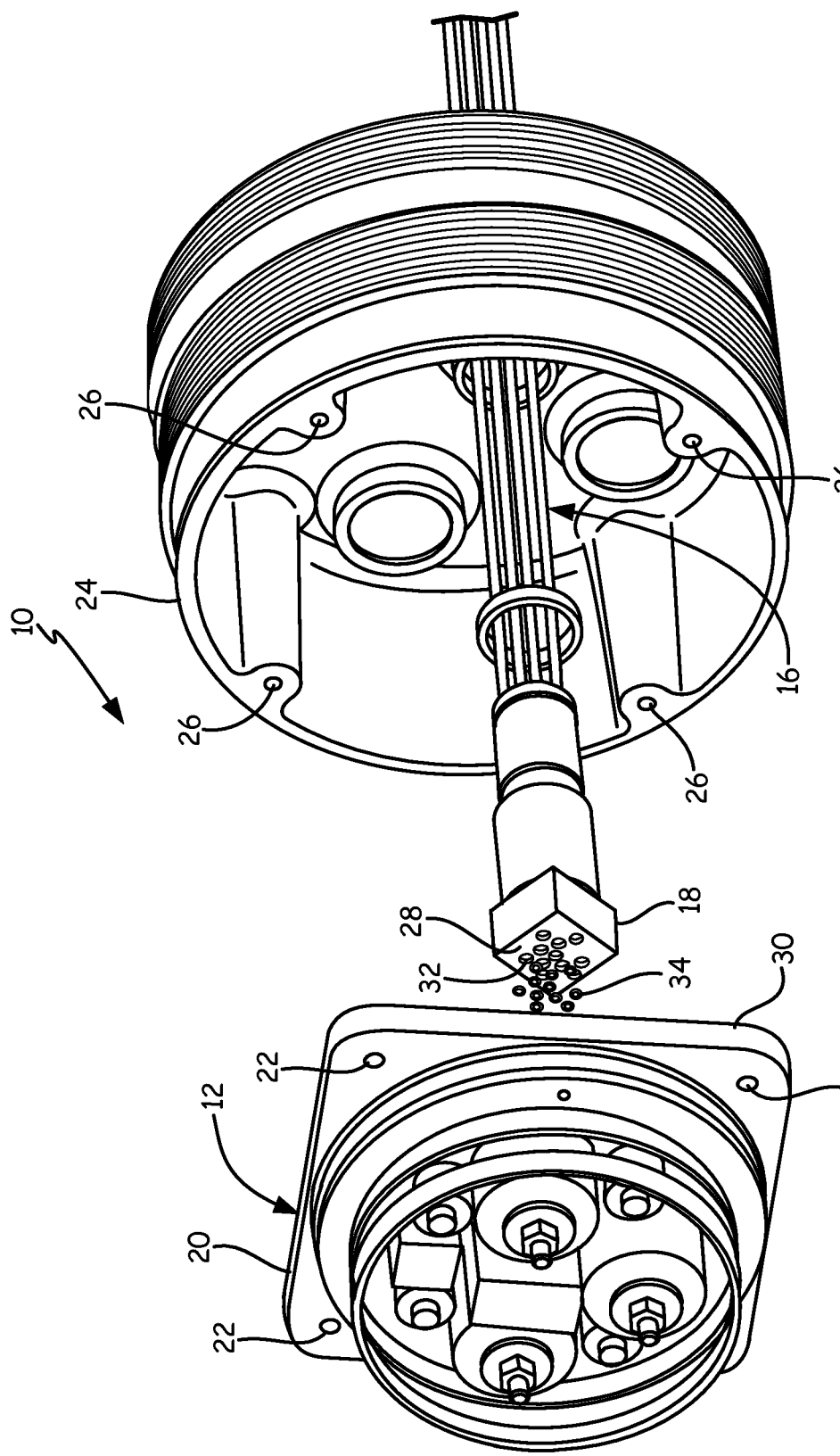
FIG. 1 is a diagrammatic perspective view of a process analytic instrument with which embodiments of the present invention are particularly useful.

FIG. 1 is a diagrammatic perspective view of a process analytic instrument in accordance with which embodiments of the present invention are particularly useful. Process gas chromatograph (analyzer) 10 includes an analytical module 12 comprising the majority of the chromatographic mechanism for chromatograph 10. As illustrated in FIG. 1, chromatograph 10 has a plurality of tubes or conduits 16 that must be connected between module 12 and analyzer housing 24. The plurality of tubes or conduits 16 are terminated (on at least one end) with modular removable tube carrier 18 that facilitates rapid and secure replacement of chromatographic analytical module 12. This provides for coupling multiple tubes or conduits between analyzer housing 24 and module 12 in a manner that does not use individual tube fittings. Moreover, utilization of modular tube carrier 18 provides for positive sealing of multiple tubes or conduits 16 in assigned or preselected positions such that tubing exchange or misassignment is prevented. This helps consolidate multiple tubes or conduits into a single tube carrier where each tube or conduit has an assigned position in the tube carrier. The individual tubes or conduits are preferably sealed and potted permanently into tube carrier 18 with a flame-arresting portion 60 disposed within the potting, as will be described in greater detail with respect to FIG. 2.

Analytical module 12 includes a variety of valves, sensors, conduits and electronics appropriate for its analytical function. For example, an analytical module for a gas chromatograph may include a number of valves, heaters, chromatographic columns, sensors such as a flame ionization detector (FID) and/or thermal conductivity detector (TCD), et cetera. Embodiments where the analytical module serves a different function, such as a process gas oxygen sensor, will have different components suitable for such function. Analytical module 12 includes base plate 20 that has a number of mounting holes 22 that allow base plate 20 to be securely mounted to housing 24 via threaded holes 26. Base plate 20 is of sufficient thickness, based on the material from which it is constructed, such that it does not significantly flex as face 28 of modular tube carrier 18 is urged against sealing surface 30, shown in greater detail in FIG. 3.

As illustrated in FIG. 1, face 28 includes a number of apertures 32 that are fluidically coupled to individual tubes or conduits. While the illustrated embodiment shows face 28 having a rectangular shape, any suitable shape can be used for face 28. Disposed within or adjacent each aperture is a seal, such as an elastomeric o-ring 34. Thus, as face 28 is sufficiently urged against surface 30, seals 34 create individual seals for each tube or conduit to surface 30. This allows all fluidic connections to module 12 to be made substantially simultaneously thereby saving significant technician time.

Figure 2:
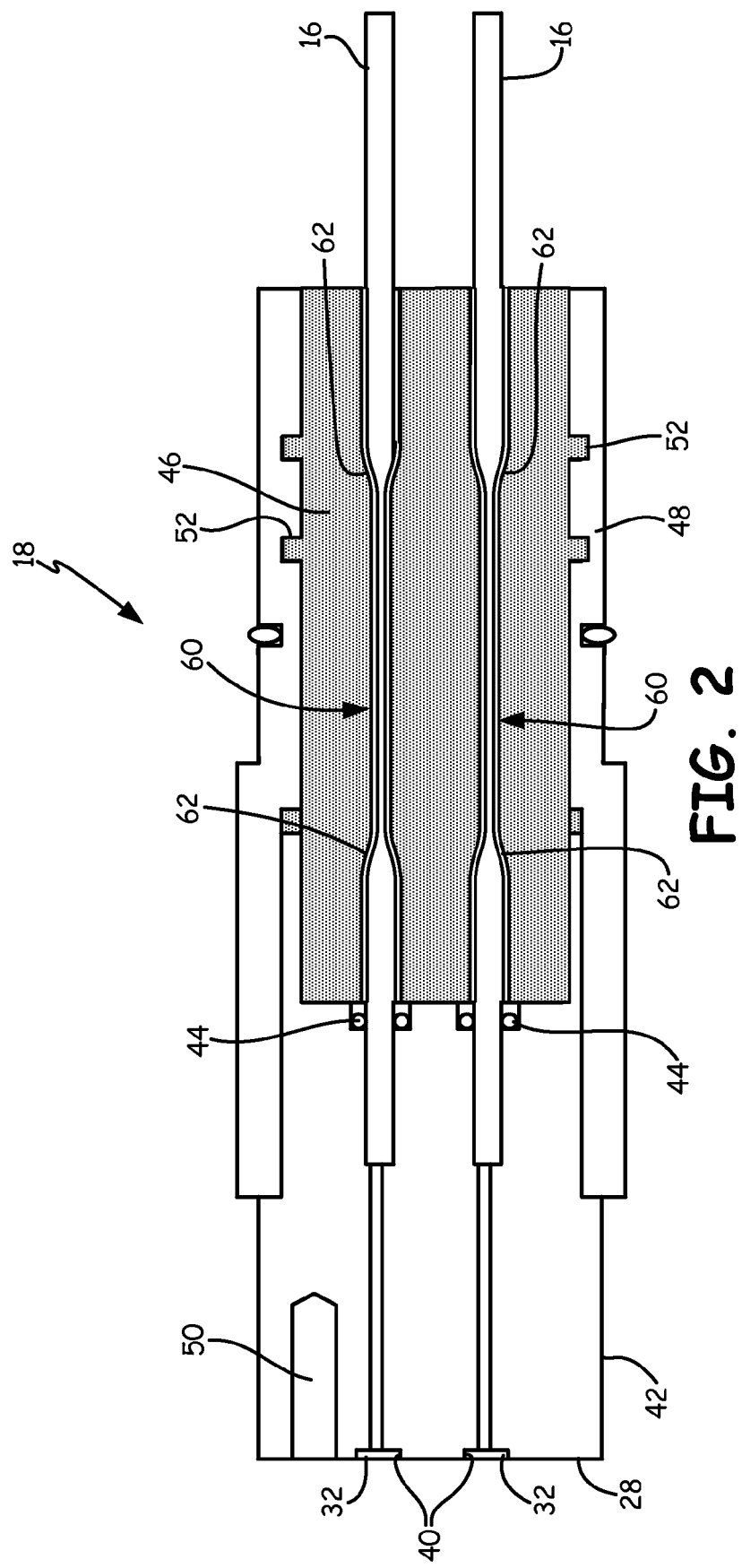
FIG. 2 is a diagrammatic cross-section of a tube carrier with a flow conduit having an encapsulated flame-quenching portion in accordance with an embodiment of the present invention.

FIG. 2 is a diagrammatic cross-section of a tube carrier in accordance with an embodiment of the present invention. End 28 of tube carrier 18 provides ports or apertures 32 associated with each tube and includes a face sealing mechanism, such as an o-ring 34 (shown in FIG. 1), for each port 32. FIG. 2 shows a pair of tubes 16 that are sealingly terminated within tube carrier 18. While FIG. 2 only shows a pair of tubes 16, in fact, any suitable number of tubes may be employed in accordance with embodiments of the present invention. Tubes 16 are fluidically coupled to carrier fitting 42 and such coupling may be facilitated using axial sealing o-rings 44, which can ensure that potting compound 46 does not leak through fitting 42 when it is injected or poured into fitting shell 48. Further, o-rings 44 can serve the additional purpose of providing a seal against any fluid leaks which might not be contained by potting compound 46. Although o-rings 44 are not relied upon to create the flameproof joint, they may be relied upon for sealing. Fitting 42 preferably includes a plurality of pin alignment holes; one of which is shown at reference numeral 50. These holes 50 cooperate with pins positioned on and extending from surface 30 of module 12 to ensure both that fitting 42 is properly oriented to surface 30 and that fitting 42 does not rotate as surface or end 28 is urged into contact with surface 30. As shown in FIG. 2, shell 48 also includes one or more internal annular grooves 52 that help retain the potting compound or glass frit within shell 48 once the compound or frit has cured or otherwise hardened.

In accordance with an embodiment of the present invention each tube 16 has a crimped, flattened, or otherwise deformed portion 60 that is sized, preferably in both the degree of deformation and the length, in order to provide requisite flame quenching functions. By virtue of portion 60, tube 16 can be considered to have an integral flame quenching pathway. While a crimp or similar deformation would normally render each tube 16 substantially weaker and more prone to damage, the encapsulation of the flame-quenching portion 60 within epoxy 46 protects crimped portion 60 from damage. Further, since crimped portion 60 has a different cross-section than the non-crimped portions of tube 16, transition areas 62 provide surfaces that cooperate with epoxy 46 to retain each tube 16 in its axial position. Thus, it is more difficult to axially slide a tube 16 having portion 60 within epoxy 46 than it would be for a non-deformed tube 16.

The provision of a flame-quenching pathway manufactured in at least one, and preferably each, tube 16 helps provide low-cost compliance with applicable industry-accepted standards from approval agencies such as CSA, UL, FM, ATEX and IEC to provide flame and explosion safe operation. The dimensions of the path and length may be varied based upon design considerations as long as they comply with applicable flameproof standards. Facilitating agency compliance is also made by the use of agency (CSA, UL, FM, ATEX, IEC, et al) compliant potting and materials 46 within shell 48, which materials help provide a flameproof seal between analyzer housing 24 and tube carrier 18.

In one embodiment, tubes 16 are formed from 1/16" diameter stainless steel tubes that are simply crimped in a crimping fixture. However, embodiments of the present invention can be practiced with other size tubes and materials. Further, while embodiments of the present invention can be practiced with a single tube being crimped or otherwise deformed to provide requisite flame quenching, it is preferred that multiple tubes be so crimped. In this way, all of the gasses entering and exiting the analytic instrument may be passed through flame arresting or quenching pathways. It is believed that in some instances, the integral flame-quenching pathways disclosed above may provide a greater amount of flow than would be provided if a flame arrestor of similar tubes with a small inner diameter were provided. Thus, the non-circular cross-section caused by the flattening of the tube is able to provide suitable flame quenching and greater flow, at less cost, than may be provided by a traditional flame arrestor.

Although the present invention has been described with reference to preferred embodiments, workers skilled in the art will recognize that changes may be made in form and detail without departing from the spirit and scope of the invention. For example, embodiments of the present invention could be applied as a flow limiting device. This would be beneficial in a situation where a dilution purge is employed as the protection scheme and quantities of explosive gasses must be limited. Additionally, embodiments of the present invention could be modified to allow for application in differing enclosures which require either a greater back-pressure along the flow path or greater flow capacity through the tube(s).

What is claimed is:

1. A process analytic instrument comprising:
   an analytic module configured to analyze a process gas, the analytic module having a plurality of inlet ports; and
   a tube carrier coupled to the analytic module, the tube carrier having a shell defining an interior therein;
   a plurality of tubes terminating in the tube carrier, wherein each of the plurality of tubes is sealed into the tube carrier, and wherein at least one of the plurality of tubes has an integral flame-quenching pathway; and
   wherein an interior of the shell proximate the integral flame-quenching pathway is filled with a solid.

2. The process analytic instrument of claim 1, wherein the process analytic instrument is a gas chromatograph.

3. The process analytic instrument of claim 1, wherein each of the plurality of tubes includes an integral flame-quenching pathway.

4. The process analytic instrument of claim 1, wherein the flame-quenching pathway is a crimped portion.

5. The process analytic instrument of claim 1, wherein a degree of crimping and length of the pathway is selected to provide flame quenching.

6. The process analytic instrument of claim 1, wherein at least one of the plurality of tubes is constructed from stainless steel.

7. The process analytic instrument of claim 1 and further comprising an elastomeric o-ring disposed about each of the plurality of tubes as each tube terminates within the tube carrier.

8. The process analytic instrument of claim 1, wherein the solid is epoxy.

9. The process analytical instrument of claim 1, wherein each of the plurality of tubes is potted permanently into the tube carrier, such that the flame-quenching pathway is within the potting solid.

10. A tube carrier for coupling a plurality of tubes to an analytical module of an analytic instrument, the tube carrier comprising:
    a shell defining an interior therein;
    a plurality of tubes terminating in the tube carrier, wherein at least one of the plurality of tubes has a deformed portion configured to provide an integral flame-quenching pathway; and
    wherein an interior of the shell proximate the integral flame-quenching pathway is filled with a solid.

11. The tube carrier of claim 10, wherein each of the plurality of tubes includes an a deformed portion configured o provide an integral flame-quenching pathway.

12. The tube carrier of claim 10, wherein the deformed portion is a crimped portion.

13. The tube carrier of claim 12, wherein a degree of crimping and length of the pathway is selected to provide flame quenching.

14. The tube carrier of claim 10, wherein at least one of the plurality of tubes is constructed from stainless steel.

15. The tube carrier of claim 10, and further comprising an elastomeric o-ring disposed about each of the plurality of tubes as each tube terminates within the tube carrier.

16. The tube carrier of claim 10, wherein the solid is epoxy.

17. The tube carrier of claim 10, wherein the solid is configured to retain each tube in an axial position.

18. The tube carrier of claim 10, wherein the solid is configured to protect the deformed portion from damage.

* * * * *